United States Patent [19]

Miyata et al.

[11] Patent Number: 5,046,842
[45] Date of Patent: Sep. 10, 1991

[54] MIXING RATIO DETECTING DEVICE FOR COMPOSITE LIQUID

[75] Inventors: Shigeru Miyata; Yoshitaka Yamada, both of Nagoya, Japan

[73] Assignee: NGK Spark Plug Co., Ltd., Nagoya, Japan

[21] Appl. No.: 626,024

[22] Filed: Dec. 12, 1990

[30] Foreign Application Priority Data

Dec. 15, 1989 [JP] Japan ................................. 1-326585

[51] Int. Cl.⁵ ............................................ G01N 21/42
[52] U.S. Cl. ..................................... 356/136; 356/133
[58] Field of Search ............... 356/128, 133, 135, 136, 356/436

[56] References Cited

U.S. PATENT DOCUMENTS 4,749,274 6/1988 Aoki et al. ........................... 356/136
4,962,746 10/1990 Miyata et al. ........................ 356/136

Primary Examiner—F. L. Evans
Attorney, Agent, or Firm—Cooper & Dunham

[57] ABSTRACT

A mixing ratio detecting device for composite liquid has a transparent column placed so that a bottom of the column is in contact with a mixing liquid, and a light emitting diode disposed so that light beams therefrom are incident on one side of the column to pass therethrough so as to impinge on an interface between the bottom of the column and the mixing liquid. The light beams impinged on the interface less than a critical angle are refracted, while the light beams impinged on the interface more than the critical angle totally reflected to escape from other side of the column. A photo diode is provided to receive the light beams escaped from the other side of the column so as to generate an output. An effective photo-receiving area of the photo diode is in the form of an inversed trapezoid to compensate for characteristics of the output from the photo diode.

3 Claims, 5 Drawing Sheets

MIXING RATIO DETECTING DEVICE FOR COMPOSITE LIQUID

BACKGROUND OF THE INVENTION

1. Field of the Invention

This invention relates to a mixing ratio detecting device which is capable of optically deteoting a mIxing degree of a liquid consisting of two components, and particularly concerns to a mixing ratio detecting device suited for detecting a mixing degree of gasoline and alcohol.

2. Description of Prior Art

In an internal combustion engine, a liquid fuel consisting of gasoline and alcohol has been suggested to adopt so as to alleviate a controversial air-pollution. In the internal combustion engine of this type, it is necessary to detect a mixing ratio of the gasoline and alcohol so as to determine an optimum timing of ignition. In cope with the requirement, a mixing ratio detecting device has been introduced in which a transparent column is provided, a bottom of which is in contact with a mixing liquid of gasoline and alcohol. A light emitting diode (LED) and a photo diode is disposed in a manner to sandwich the column. Light beams from the LED passes within the column, and impinges on an interface between the column and the mixing liquid at more than a critical angle. The light beams, thus impinged on the interface at more than the critical angle, totally reflect to escape from the column so as to fall on the photo diode which generate an output in accordance with an quantity of the light beams received. In this instance, the quantity of the light beams which the photo diode receives increases with the increase of the alcohol component because the light beams from the LED lengthen its optical path to impinge on a relatively upper part of the photo diode.

However, the increased alcohol component causes to saturate output characteristics of the photo diode as shown in FIG. 6 in which depicts a graph with abscissa and ordinate as a mixing ratio and an output from the photo diode respectively. This is because the light beams from the LED diverge right and left, and the diverging degree increases as the optical path lengthens which is equivalent to a travel length required for the light beams to reach the photo diode throught the colúmn.

This requires a complicate procedure to treat the output from the photo diode in obtaining a precise mixing ratio of gasoline and alcohol, and rendering it difficult to carry out a temperature compensation easily.

Therefore, it is an object of the invention to provide a mixing ratio detecting device for composite liquid which is capable of easily compensating for output characteristics from a photo diode, and always securing a precise mixing ratio with a simple construction.

SUMMARY OF THE INVENTION

According to the invention, there is provided a mixing ratio detecting device for composite liquid comprising; an optically permeable column placed so that a bottom of the column is in contact with a mixing liquid, a refractive index of which is smaller than that of the column; a light emitting diode disposed so that light beams therefrom are incident on one side of the column to pass therethrough so as to impinge on an interface between the bottom of the column and the mixing liquid, the light beams impinged on an interface less than a critical angle being refracted to the mixing liquid, while the light beams impinged on an interface more than the critical angle being totally reflected therefrom to pass within the column, and escape from other side of the column, the critical angle depending on a mixing degree of the liquid: a photo diode provided to receive the light beams escaped from the other side of the column so as to generate an output in accordance with the quantity of the light beams received; an effective photo-receiving area of the photo diode being shaped to progressively increase its width dimension as it is remote from the interface so as to compensate for characteristics of the output from the photo diode.

Output characteristics of the photo diode is compensated by shaping the light receiving area of the photo diode to progressively increase its width dimension as it is remote from the interface between the column and the mixing liquid. This arrangement makes it possible to enable a linear relationship between a mixing ratio of the liquid and an output from the photo diode so as to easily compensate for output characteristics from a photo diode and always securing a precise mixing ratio with a simple construction.

These and other objects and advantages of the invention will be apparent upon reference to the following specification, attendant claims and drawings.

DETAILED DESCRIPTION OF THE EMBODIMENTS

Figure 1:
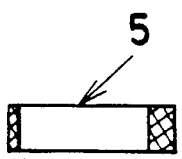
FIG. 1 is a plan view of a compensation photo diode according to the invention.
Figure 1A:
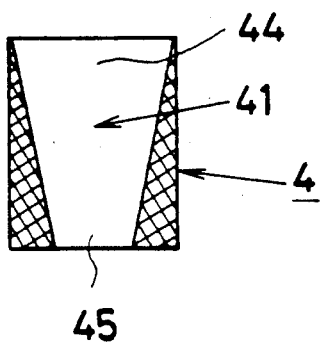
FIG. 1a is a plan view of a photo diode according to the invention.
Figure 2:
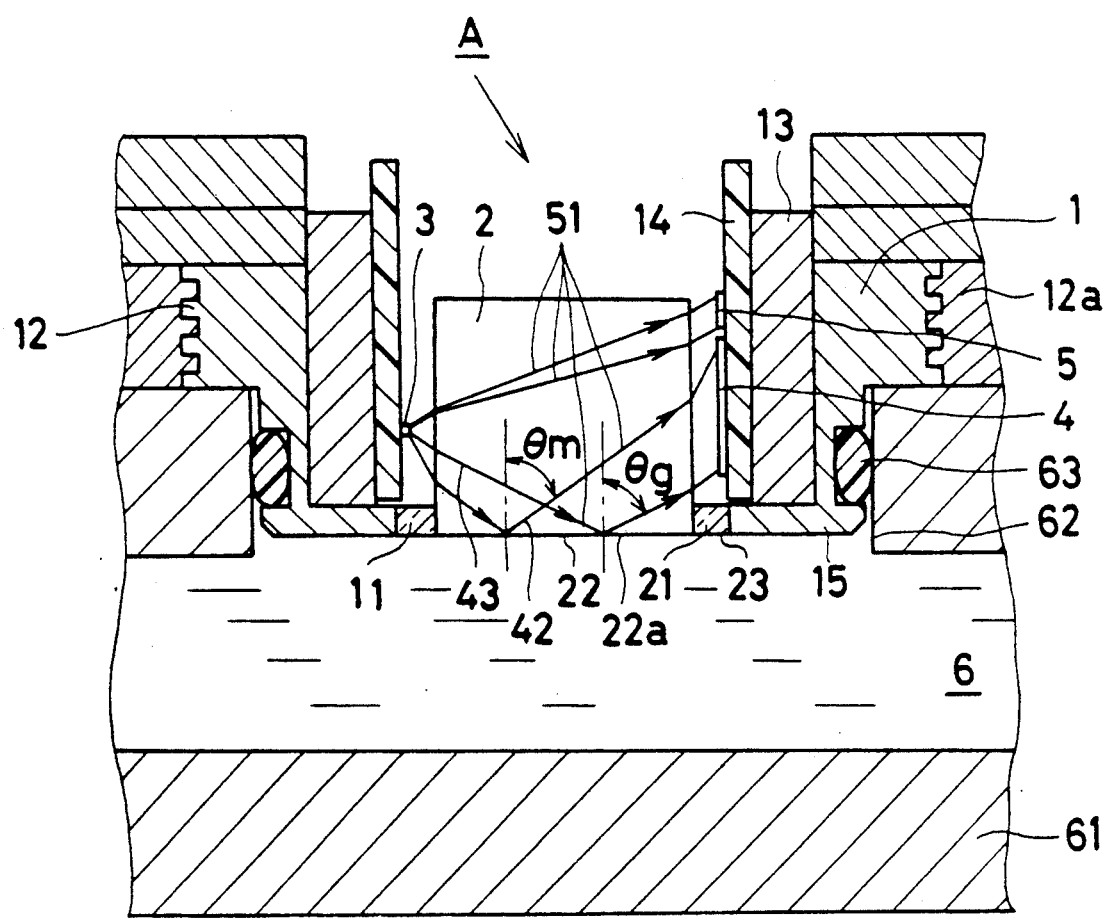
FIG. 2 is a longitudinal cross sectional view of a mixing ratio detecting device according to the invention.

Referring to FIGS. 1 through 5 in which an embodiment of the invention is shown, a compensation photo diode 5 and a photo diode 4 each shown in FIGS. 1, 1a are incorporated into a mixing ratio detecting device (A). As shown in FIG. 2, the device (A) has a cylindrical holder 1 which is, by way of an O-rIng 63, liquid-tightly interfit into a circumferential periphery of an aperture 62 provided with a metallic pipe 61 through which a mixing liquid 6 flows. The mixing liquid 6 is a mixture of gasoline and alcohol (methanol) to serve as a liquid fuel of an internal combustion engine. The holder 1 has an serration 12 at an outer surface so as to tightly interfit into a support ring 12a fixed on the pipe 61. Into the holder 1, is a cylindrical board 14 interfit through a resinoid cylinder 13. Within the resinoid cylinder 13, is an optically permeable column 2 placed which is made of a flint glass, a refractive index (1.58) of which is greater than that of the mixing liquid 6 which is adapted to continuously change within a range from 1.33 to 1.43. Into a circumferential periphery of a circular hole 11 of the holder 1, is a bottom 22 of the optically permeable column 2 liquid-tightly interfit through a vitrified ring 21 to be in contact with the mixing liquid 6 at an interface 22a. In this instance, a bottom 15 of the holder 1 and a bottom 23 of the vitrified ring 21 are in flush with the of bottom 22 of the column 2.

Figure 1B:
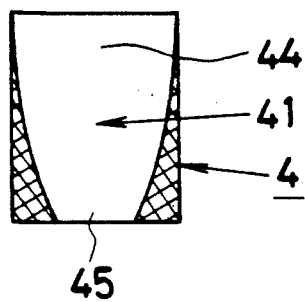
FIG. 1b is a plan view of a photo diode according to a modified form of the invention.

In the meanwhile, a light emitting diode (LED) 3 and a photo diode 4 are attached to an inner surface of the cylindrical board 14 in a manner to sandwich the column 2. An effective photo-receiving area 41 of the photo diode 4 is designed in the form of an inversed trapezoid to have an upper area portion 44 and a lower area portion 45 by partly masking the photo diode 4 as shown at meshes in FIG. 1a. This means that the photo-receiving area 41 is shaped to progressively increase its width dimension as it is remote from the interface 22a so as to compensate for characteristics of the output from the photo diode 4. In this instance, the photo diode 4 is partly masked to be contoured along a conic section as shown in FIG. 1b which is as a modified form of the invention.

A compensation photo diode 5 is attached to the inner surface of the cylindrical board 14 in an up-and-down relationship with the photo diode 5. The compensation photo diode 5 is adapted to always receive a certain quantity of the light beams 51 from the LED 3 directly passing through the column 2, and incorporated into a voltage stabilizing circuit shown in FIG. 2a.

Figure 2A:
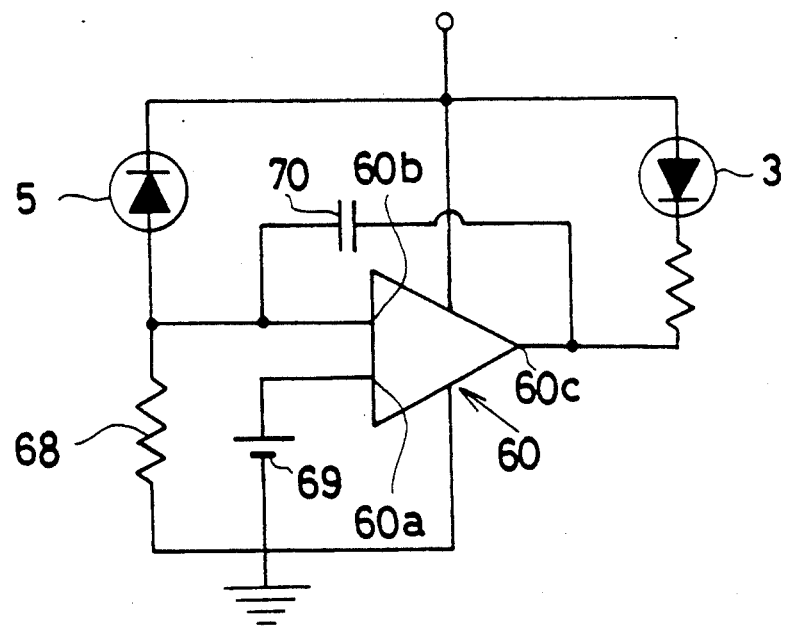
FIG. 2a is a voltage stabilizing circuit incorporated to the mixing ratio detecting device according to the invention

In the voltage stabilizing circuit in FIG. 2a, an operational amplifier 60 has an input terminal 60a which is grounded by way of a battery cell 69. Across another input terminal 60b and an output terminal 60c of the operational amplifier 60, the LED 3 is provided which is connected in series with the compensation photo diode 5. An electrical resistor 68 is connected across the compensation photo diode 5 and the ground. A condensor 70 is connected across the input terminal 60b and the output terminal 60c of the operational amplifier 60 in order to prevent a hunting phenomenon as well known for artisans versed in the art.

In a situation in which the device (A) is placed, the LED 3 and the photo diode 4 are subjected to variation of their characteristics depending on the ambient temperature or their ageing. The variation of the ambient temperature causes to change the light beams from the LED 3.

In accompany with the variation of the ambient temperature, the quantity of the light beams which the photo diode 5 receives occurs so as to change the output generated therefrom. A decrease of a current flowing through the compensation photo diode 5 causes to decrease a current flowing through the electrical resistor 68. That is, the current flowing through the compensation photo diode 5 is compensated by the increase of current across the LED 3, so that the light emitting degree from the LED 3 is generally maintained uniform irrespective of the variation of the ambient temperature.

In operation, the light beams from the LED 3 are incident on one side of the column 2 to pass therethrough so as to impinge on the interface 22a between the bottom 22 of the column 2 and the mixing liquid 6. The light beams impinged on the interface less than a critical angle are refracted to a side of the mixing liquid 6, while the light beams impinged on the interface more than the critical angle totally reflected therefrom to pass within the column 2, and escape from other side of the column 2. The critical angle changes depending on a mixing degree of the mixing liquid 6.

Figure 3:
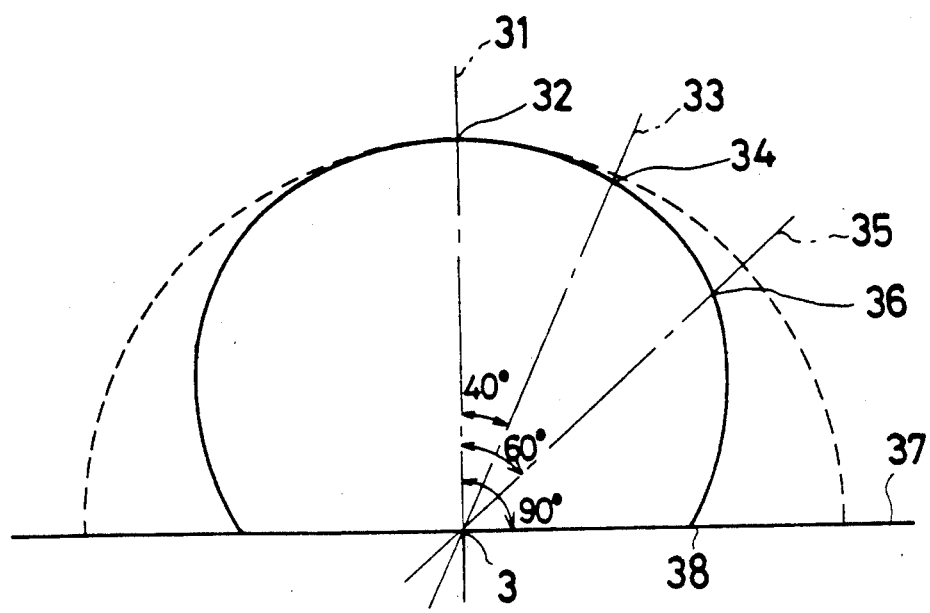
FIG. 3 is a schematic graph showing diverging characeristics of the photo diode.

In this instance, when a quantity of the light beams 31 from the LED 3 directed perpendicular to the photo diode 4 is 100 % as designated at 32, an quantity of the light beams 33 diverted by 40 degrees from the perpendicular line decreases to 95 % as indicated at 34 in FIG. 3 which shows the light beams from the LED 3 diverge depending on angles diverted from the line perpendicular to the photo diode 4. The diverging degree of the light beams from the LED 3 tends to increase with the increase of an optical path which the light beams travel within the column 2. On the other hand, a quantity of the light beams 35 diverted by 60 degrees from the perpendicular line decreases to 80 % as indicated at 36. Similarly a quantity of the light beams 37 diverted by 90 degrees from the perpendicular line drops to 60 % as indicated at 38.

When the gasoline component of the mixing liquid 6 is 100 %, the total reflection from the interface 22a occurs at an angle of more than the critical angle ($\theta g$). In this instance, the light beams from the LED 3 has an angular divergenoe equivalent to the case in which the quantity of the lIght beams 33 diverted by circa 40 degrees from the perpendicular line decreases to about 95 % as indicated at 34 in FIG. 3.

When the alcohol component of the mixing liquid 6 is 100 %, the total reflection from the interface 22a occurs at an angle of more than the critical angle ($\theta m$). In this instance, the light beams from the LED S has an angular divergence equivalent to the case in which the quantity of the light beams 35 diverted by circa b 60 degrees from the perpendicular line decreases to about 80 % as indicated at 36 in FIG. 3.

On the other hand, an optical path 42 when the light beams totally reflected at the critical angle ($\theta m$) becomes longer than an optical path 43 when the light beams totally reflected at the critical angle ($\theta g$), so that the diverging degree of the light beams from the LED 3 increases in the latter case as seen in FIG. 2.

As understood from the foregoing description, the effective photo-receiving area 41 of the photo diode 4 is designed in the form of the inversed trapezoid which has the upper area portion 44 and the lower area portion 45. The upper area portion 44 works to compensate the quantity of the lIght beams received by the enlarged area of the upper area portion 44 when the light beams impinged on the upper area portion 44 decrease due to the divergence of the light beams from the LED 3.

Figure 4:
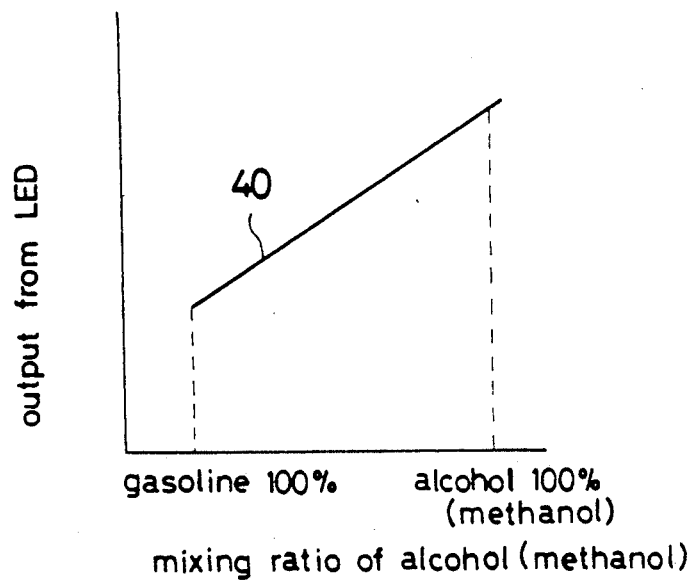
FIG. 4 is an output characteristics showing a relationship between an output and a mixing ratio of gasoline and alcohol.
Figure 5:
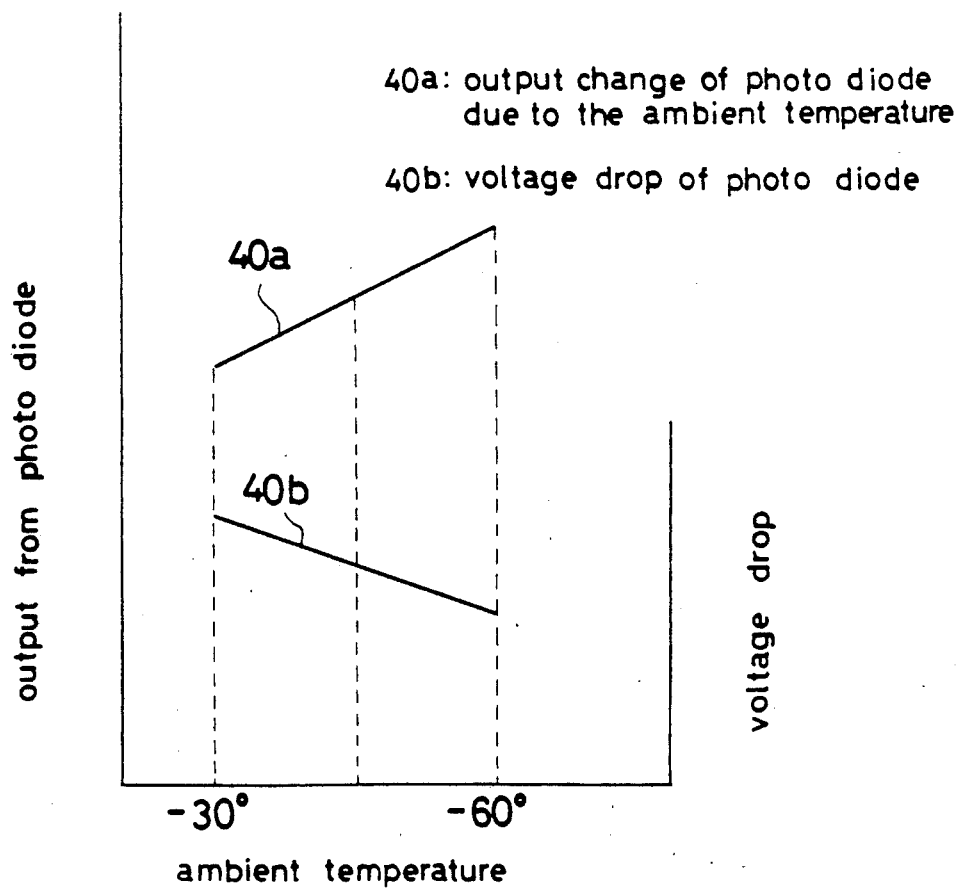
FIG. 5 is a characteristic graph showing how to carry out a temperature compensation.
Figure 6:
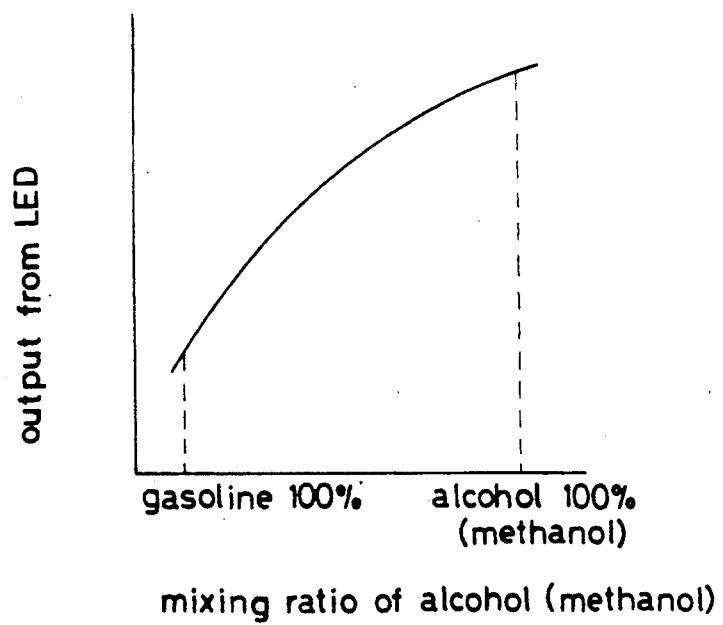
FIG. 6 is a graph showing a relationship with abscissa and ordinate as a mixing ratio and an output from the photo diode respectively.

Therefore, output characteristics 40 of the LED 3 is as shown in FIG. 4 in which an output from the LED 3 linearly changes with a mixing ratio of alcohol under a constant temperature.

In the meanwhile, the refractive index of the mixing liquid 6 changes at the rate of circa $-4 \times 10^{-4}$/C with the increase of the ambient temperature. As a result, the quantity of the light beams which the photo diode 4 receives increases with the increase of the ambient temperature so as to increase the output therefrom. The output change generated from the photo diode 4 is in a linear relationship with the change of the ambient temperature as shown at 40a in FIG. 8 since the output from the LED 3 linearly changes with the mixing ratio of alcohol. The output from the photo diode 4 is adapted to be transmitted to a central processing unit (not shown) so as to control an optimum timing of an ignition for the internal combustion engine.

In a situation in which the device (A) is placed, the LED 3 is subjected to variation of its output characteristics depending on the ambient temperature. The increased ambient temperature causes to decrease an electrical resistant value of the LED 3 so as to drop a voltage across the LED 3 as shown at 40*b* in FIG. 5. The change of the ambient temperature is, in some degree, compensated by the voltage drop across the LED 3 so as to somewhat cancel the output change from the photo diode 4.

It is noted that the shape of the photo diode is easily determined when an angle incident on the photo diode is adapted to continuously change with the change of a reflective angle from the interface.

It is appreciated that the optically permeable column may be circular, rectangular or polygonal in section.

Further, the change the refractive index of the gasoline according to the ambient temperature is slightly different from that of the alcohol, and the former is more than the latter to define precisely. In this case, the shape of the photo diode may be determined so that the output characteristics 40 in FIG. 4 curves somewhat downward in order to secure a more precise compensation effect.

While the invention has been described with reference to the specific embodiments, it is understood that this description is not to be construed in a limitting sense in as much as various modifications and additions to the specific embodiments may be made by skilled artisan without departing from the spirit and scope of the invention.

What is claimed is:

1. A mixing ratio detecting device for composite liquid comprising;
    an optically permeable column placed so that a bottom of the column is in contact with a mixing liquid, a refractive index of which is smaller than that of the column;
    a light emitting diode disposed so that light beams therefrom are incident on one side of the column to pass therethrough so as to impinge on an interface between the bottom of the column and the mixing liquid, the light beams impinged on the interface less than a critical angle being refracted to the mixing liquid, while the light beams impinged on the interface more than the critical angle being totally reflected therefrom to pass within the column, and escape from other side of the column, the critical angle depending on a mixing degree of the liquid;
    a photo diode provided to receive the light beams escaped from the other side of the column so as to generate an output in accordance with the quantity of the light beams received:
    an effective photo-receiving area of the photo diode being shaped to progressively increase its width dimension as it is remote from the interface so as to compensate for characteristics of the output from the photo diode.

2. In a mixing ratio detecting device for composite liquid as recited in claim 1, the effective photo-receiving area of the photo diode is in the form of an inversed trapezoid.

3. In a mixing ratio detecting device for composite liquid as recited in claim 1, the mixing liquid is a mixture of gasoline and alcohol.

* * * * *